(12) United States Patent
Shah et al.

(10) Patent No.: US 11,596,491 B2
(45) Date of Patent: Mar. 7, 2023

(54) MAGNETIC TUBING HOLDER

(71) Applicant: Beckman Coulter, Inc., Brea, CA (US)

(72) Inventors: Sarang Shah, Miami, FL (US); Francisco Bolanos, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 11 days.

(21) Appl. No.: 16/210,692

(22) Filed: Dec. 5, 2018

(65) Prior Publication Data

US 2020/0179074 A1   Jun. 11, 2020

(51) Int. Cl.
| | |
|---|---|
| *A61B 50/20* | (2016.01) |
| *A61M 39/08* | (2006.01) |
| *F16L 3/12* | (2006.01) |
| *A61B 50/18* | (2016.01) |
| *A61B 50/10* | (2016.01) |

(52) U.S. Cl.
CPC ............ *A61B 50/20* (2016.02); *A61M 39/08* (2013.01); *F16L 3/1222* (2013.01); *A61B 2050/105* (2016.02); *A61B 2050/185* (2016.02); *A61B 2050/21* (2016.02)

(58) Field of Classification Search
CPC ............ A61B 50/20; A61B 2050/105; A61B 2050/185; A61M 39/08; F16L 3/1222
See application file for complete search history.

(56) References Cited

U.S. PATENT DOCUMENTS

| | | | | |
|---|---|---|---|---|
| 9,695,394 | B1 * | 7/2017 | Coelho | ............... C12M 23/44 |
| 2003/0014035 | A1 * | 1/2003 | Trombley | ............. A61M 5/142 |
| | | | | 604/500 |
| 2010/0159741 | A1 * | 6/2010 | Rothbaum | ............. F16G 11/00 |
| | | | | 439/501 |
| 2014/0020928 | A1 * | 1/2014 | Johnson | ............... H02G 11/006 |
| | | | | 174/110 R |
| 2014/0033394 | A1 * | 2/2014 | Stauffer | ................ H01F 7/0263 |
| | | | | 2/69 |
| 2017/0035522 | A1 * | 2/2017 | Roland | .................. A61B 50/22 |

OTHER PUBLICATIONS

Source, Magnetic Clip, Jun. 28, 2010 YouTube, https://www.youtube.com/watch?v=hSNwNyJSvV4, (Year: 2010).*

* cited by examiner

*Primary Examiner* — Kimberly T Wood
(74) *Attorney, Agent, or Firm* — Schwegman Lundberg & Woessner, P.A.

(57) ABSTRACT

Embodiments of the present disclosure relate generally to a holder for medical tubing. Specific embodiments find particular use in managing reagent replacement tubes which are often used in connection with various types of types of laboratory equipment. In a specific example, one or more magnets are associated with the reagent tubing. The one or more magnets are used to secure the reagent tubing to a portion of the equipment stand or base, the drawer, or any other magnetically responsive surface.

13 Claims, 7 Drawing Sheets

MAGNETIC TUBING HOLDER

FIELD OF THE DISCLOSURE

Embodiments of the present disclosure relate generally to a holder for medical tubing. Specific embodiments find particular use in managing reagent replacement tubes which are often used in connection with various types of laboratory equipment.

BACKGROUND

During operation of various types of laboratory equipment, is often the case that one or more reagents or diluents will need to be replaced. For example, body fluid analyzers (such as hematology analyzers, urinalysis equipment, or other types of body fluid analyzers or instruments) may receive an input of the body fluid and run various tests in order to collect accurate data about individual cell size, shape, structure, and count. These analyzers may operate via electrical impedance, flow cytometry, fluorescent flow cytometry, imaging, or various other methods. The analyzers are generally used in combination with one or more chemical reagents and/or diluents that dilute, lyse, facilitate cell flow, or otherwise prepare the body fluid to be analyzed.

As illustrated by FIG. 1, the chemical reagents and/or diluents (collectively referred to herein as "reagents") may be provided in containers 10 that are housed on or near the equipment in which they are used. In some examples, the containers 10 may be housed in drawers 12 or shelves associated with the equipment stand or base 14. During operation of such types of laboratory equipment, there is often a need to replace and/or change the reagents used. This is accomplished by removing reagent tubing 16 from the container 10 currently in use (but that has been emptied, has expired, etc.), and removing and replacing the used container 10 with a replacement container.

BRIEF SUMMARY

As replacement of used reagent containers occurs, lab technicians are challenged with managing the associated tubing. It is generally undesirable for the tubing to dangle and touch the floor or other surfaces (as shown by prior art FIG. 1), because this can result in contamination of the tubing with dust, dirt, or other types of foreign particles. Such contamination can, in turn, result in the intake of particles with the reagent, causing the body fluid analyzer equipment to mistakenly recognize a contamination particle as a blood cell component or other body fluid particle or component, leading to potentially erroneous or otherwise unreliable results. Particle contamination could clog small tubes, needle lumens, flowcell pathways, or other passageways within the instrument, or could obstruct or interfere with lights or light sensors used for analysis. Challenges with tubing management may also lead to tangled tubing that can interfere with the reagent containers.

Embodiments of this disclosure thus provide a reagent tubing management solution. The tubing management solution disclosed allows temporary anchoring of the tubing while reagent containers are changed. It also allows the tubing to be easily retrievable for further use after the reagent placement process has been completed. Proper anchoring of the reagent tubing can help prevent potential contamination of the instrument, as well as ease lab personnel processes.

In a specific example, one or more magnets are associated with the reagent tubing. The one or more magnets may be positioned anywhere along the tubing. In a specific example, the one or more magnets may be positioned at Y portion of the tubing. In another example, the one or more magnets are positioned at the tail end of the tubing, along the tubing body, at the Y portion of the tubing, or any combination thereof. In an alternate example, one or more magnets could be positioned on the cap of the reagent container. The one or more magnets are used to secure the reagent tubing (or, if positioned on the cap of the reagent container, indirectly secure the tubing) to a portion of the equipment stand or base, the drawer, or any other magnetically responsive surface.

In one embodiment, there is provided a tubing management system, comprising: a length of tubing associated with laboratory equipment; and at least one magnet associated with the length of tubing. The magnet may be a ring magnet. The tubing may have a Y-portion that connects an equipment line tubing with one or more reagent connection lines, and wherein the magnet is positioned at or near the Y-portion. The magnet may be positioned anywhere along the length of tubing, at an end of the length of tubing, at a Y-portion of the tubing, or any combination thereof. It is possible to provide a protective covering over the magnet. In a specific example, the covering may be a heat shrink sleeve.

In use, the tubing management system is configured to allow a user to securely anchor the tubing to a magnetically responsive surface. It is possible for the length of tubing to be secured only by the magnets and not via a clamp or a hook associated with the equipment. The magnetically responsive surface can be a portion of an equipment stand or base, a drawer, stand doors, a benchtop, a keyboard tray, or a portion of magnetically responsive material secured to or associated with a surface. The magnetic surface may be an inherent magnetic surface of the housing for the instrument. In an alternate embodiment, the magnetic surface may be a separate magnetically responsive portion of material secured to a surface of the housing. The magnetically responsive surface may have an indicator (to show where the magnet may be placed for use).

There may be an indirect association between the tubing and the magnet, such that the magnet is positioned on the cap of the reagent container and is associated with the length of tubing when the cap is on the reagent container. In other examples, the magnet is secured directly to a magnetically responsive receiving surface of the equipment. There may be a single magnet or two or more magnets along the length of tubing.

Other embodiments provide a tubing management system, comprising: a length of tubing associated with laboratory equipment; a ring magnet associated with the length of tubing; and a protective covering comprising a heat shrink sleeve positioned over the magnet, wherein the tubing comprises a Y-portion that connects an equipment line tubing with one or more reagent connection lines, and wherein the ring magnet is positioned at or near the Y-portion.

Further embodiments provide a method for tubing management for a laboratory instrument positioned on or within an instrument housing, the method comprising: providing one or more reagent containers; providing reagent container tubing with one or more magnets associated with the tubing; providing a magnetic surface to attach the magnet to; placing the magnet such that a length of the tubing between an instrument connection and the magnet is sufficient to reach the magnetic surface; placing the magnet "at" a y-portion such that one or both reagent containers connected by the y can be replaced without disturbing the other container; placing the magnet such that a length of the tubing between the magnet and the connection to the reagent container is less than a distance between the magnetic surface and the floor. Other options and examples are described further herein.

DETAILED DESCRIPTION

Figure 2:
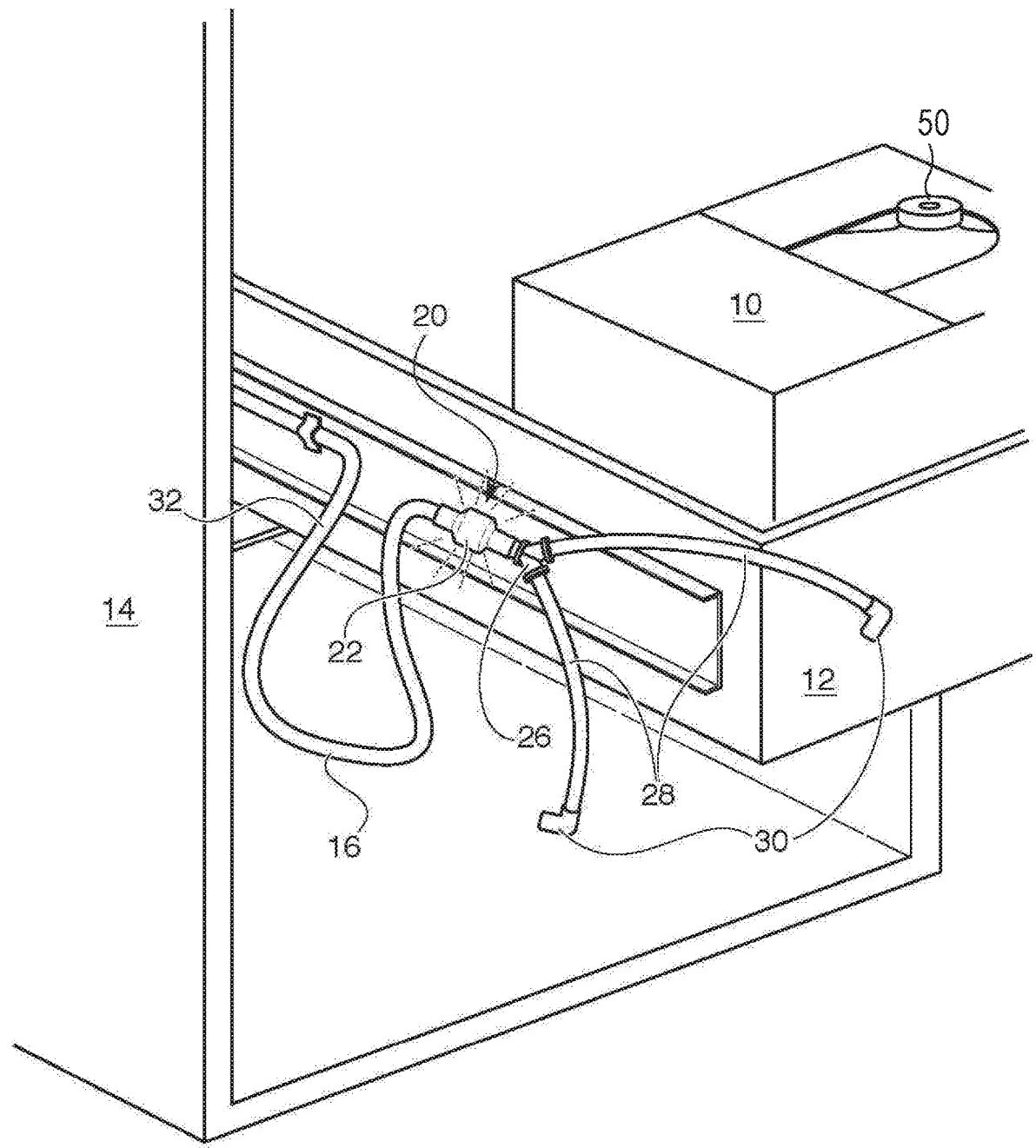
FIG. 2 shows a side perspective view of a magnetic tubing management system in use on reagent tubing.
Figure 3:
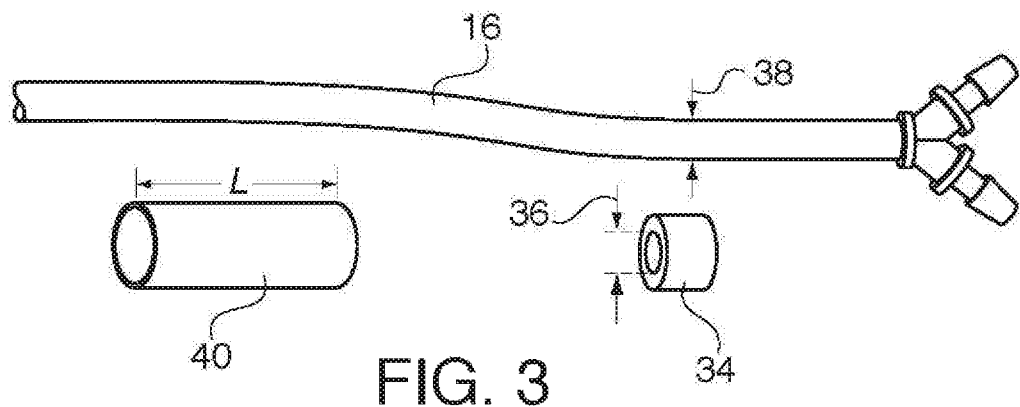
FIG. 3 shows a side perspective exploded view of reagent tubing, a ring magnet, and a protective covering, prior to assembly.
Figure 4:
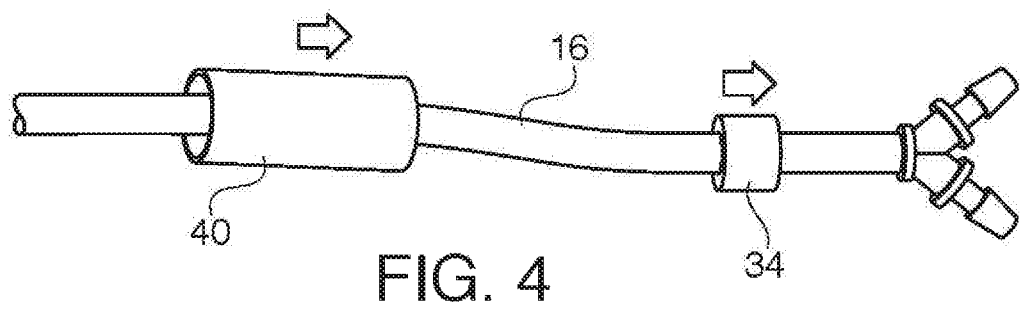
FIG. 4 shows the components of FIG. 3 during assembly.

Embodiments of the present disclosure provide a tubing management system 20. The tubing management system 20 is designed to allow a user to secure reagent tubing 16 to a portion of the equipment stand or base 14, the drawer 12, stand doors, a benchtop, keyboard tray, or any other magnetically responsive surface nearby. Exemplary magnetically responsive services are surfaces that are magnetic, or that have been energized to become a magnetic plate and can receive and secure a magnet thereto. As illustrated by FIGS. 2-4, the tubing management system 20 incorporates one or more magnets 22 associated with the tubing 16. The one or more magnets 22 are used to secure the reagent tubing 16 to a nearby magnetically responsive surface 24.

Figure 1:
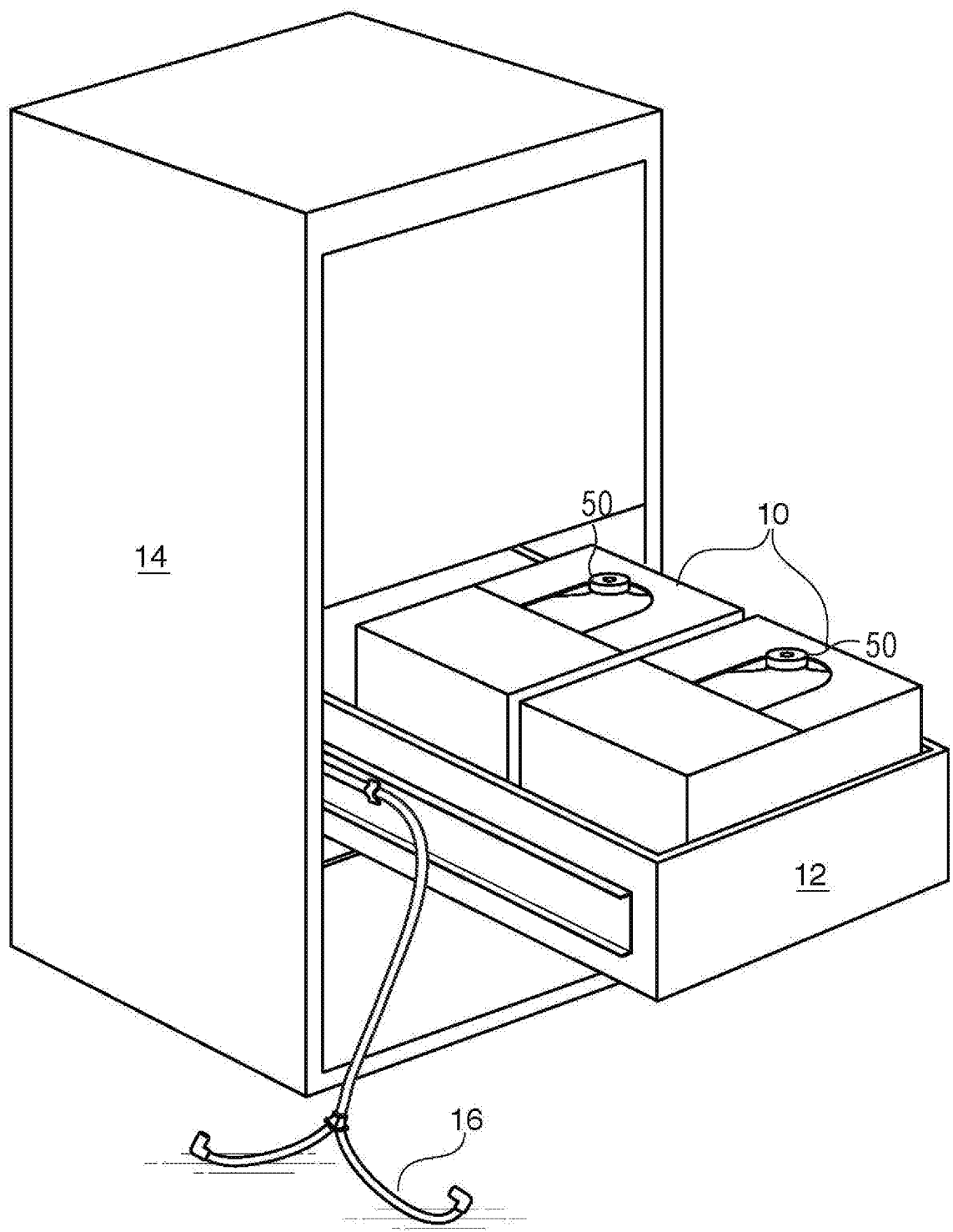
FIG. 1 shows a prior art illustration of dangling reagent tubing during changing of reagent containers.

In the specific embodiment illustrated by FIG. 2, a magnet 22 is positioned along a tubing portion that is near a Y-portion 26 of the tubing line. This location has been found to be useful in securing the tubing 16 for two reagents containers 10 in place with only a single magnet. As background, many laboratory instruments use multiple reagent containers 10. In some instances, reagent containers 10 contain different agents that are mixed at the point of use. In other instances, reagent containers 10 may be duplicates and provided in multiples in order to increase equipment capacity and running time. Accordingly, reagent tubing 16 may include multiple reagent connection lines 28 with reagent connectors 30 at the ends thereof. Two reagent connection lines 28 are illustrated by FIGS. 1 and 2, but it should be stood that more than two reagent connection lines 28 are possible and considered within the scope of this disclosure. The multiple reagent connection lines 28 may branch from a Y-portion 26. This allows a single equipment line 32 to be fed by more than one reagent container. Positioning the magnet 22 at or near the Y-portion 26 allows a single magnet 22 to securely anchor more than one reagent connection line 28. FIG. 2 illustrates the magnet 22 positioned at the base of the Y portion 26.

It should be understood, however, that a separate magnet may be provided anywhere along or at the end of each reagent connection line 28 in order to allow separate and independent anchoring of the separate and independent reagent connection lines 28. For example, a magnet may be provided at the tail end of the tubing. This could, for example, facilitate changing only one of two or more reagent containers 10, such as when a first reagent container is nearly empty, and a second reagent container is providing reagent to the instrument.

FIG. 3 illustrates the magnet used as being a ring magnet 34. It has been found that use of a ring magnet 34 encircles the entirety of the tubing 16 and provides a circumference of magnetic force. This allows ease of placement/securement of the tubing 16 in use, such that any area around the circumference of the tubing has magnetic force. In a specific example, the ring magnet 34 used may have an inner diameter 36 (ID) that is only slightly larger than or equal to the outer diameter 38 (OD) of the tubing 16. In this instance, the ring magnet 34 may be friction fit onto the tubing. In a specific example, the OD of the tubing may be about ¼" (approximately 0.64 cm) or about ⅜" (approximately 0.95 cm), and the ID of the ring magnet 34 may be correspondingly similar. Different reagent containers 10 could be connected using differently sized tubing, with ring magnets 34 sized to each tube.

It should be understood, however, that one or more flat magnets, one or more square magnets, magnetic particles, one or more flexible or strip magnets, or any other type of magnet or combination thereof may be used and is considered within the scope of this disclosure. It is also possible for the tubing itself to be made magnetic, of a magnetic material, embedded with magnetic particles, or otherwise directly exhibit magnetic features. Good anchoring results may be achieved by use of new and stronger magnets currently available. Non-limiting examples of potential magnets resulting in positive anchoring results as described herein include the use of ring magnets manufactured and sold by Master Magnets, Inc., MagnetSource.com, or fastenal.com. One example is a ring magnet having an ½" OD×¼" ID×⅜"HIGH, 13 lb-Pull Super Ring Neodymium Magnet. Nickel plated magnets may be useful as they are less prone to rust or chipping than rare earth magnets. It should be understood that the magnet type, dimensions and pull may be modified and are dependent upon the tubing dimensions and weight.

Figure 5:
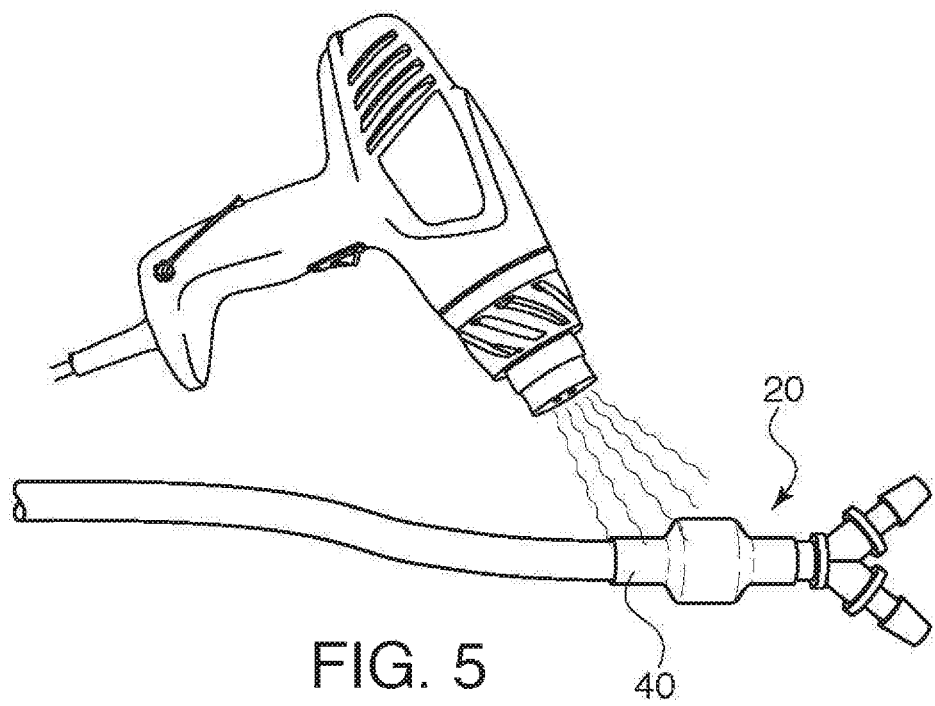
FIG. 5 shows a side perspective view of heat treatment being applied to a heat shrink tubing around a ring magnet positioned along reagent tubing.

Additionally, in order to prevent magnet chipping or flaking over time, which could also be a source of instrument contamination, a protective covering 40 may be associated with the magnet. In a specific example, the protective covering 40 is a sleeve positioned over the magnet. The sleeve 40 may be a tubular component having a length L that is slightly longer than the length of the magnet used. In a specific example, the sleeve 40 may be a heat shrink tubing. As illustrated by FIGS. 3-5, in one example, a ring magnet 34 and a sleeve 40 may be positioned along tubing 16. The sleeve 40 is positioned over the ring magnet 34. Application of heat causes the sleeve 40 to heat shrink around the ring magnet 34. This can provide securement of the ring magnet 34 in place around the tubing 16 by sealing the ends of the ring magnet 34 in place. This can also provide a layer of protection for the magnet to prevent chipping and/or flaking of the magnet from prolonged use. It is generally envisioned that the heat shrink sleeve can be provided in long rolls and cut to size to fit around the ring magnet 34 or whatever type of magnet is to be used.

Heat shrink tubing materials include but are not limited thermoplastic materials, such as polyolefins, fluoropolymers, PVC, neoprene, or silicone elastomers. Non-limiting examples of potential sleeve materials resulting in positive anchoring and heat shrink results as described herein include the use of the sleeve tubing manufactured and sold by cableorganizer.com. One example is a commercial grade heat shrink tubing having a ½" inner diameter. It should be understood that the sleeve tubing dimensions may be modified and are dependent upon the ring magnet and tubing dimensions. Additionally, it has been found that providing a colored material for the sleeve 40 can help identify tubing management system 20 for lab personnel, making the system easily observable so that it stands out and is more likely to be used. Use of a particular color or logo imprinted on the sleeve (or other type of printing or labeling or sticker) may also help with company branding recognition. Instructions for use may also be printed on or otherwise applied to the sleeve if deemed necessary or helpful.

It should be understood that rather than being provided as a sleeve, the protective covering 40 may be a coating that is sprayed, painted, dipped, or otherwise applied over the tubing and magnet. An exemplary coating may be a plastic-like coating, a nylon coating, a silicone coating, or any other appropriate protective material.

Figure 6:
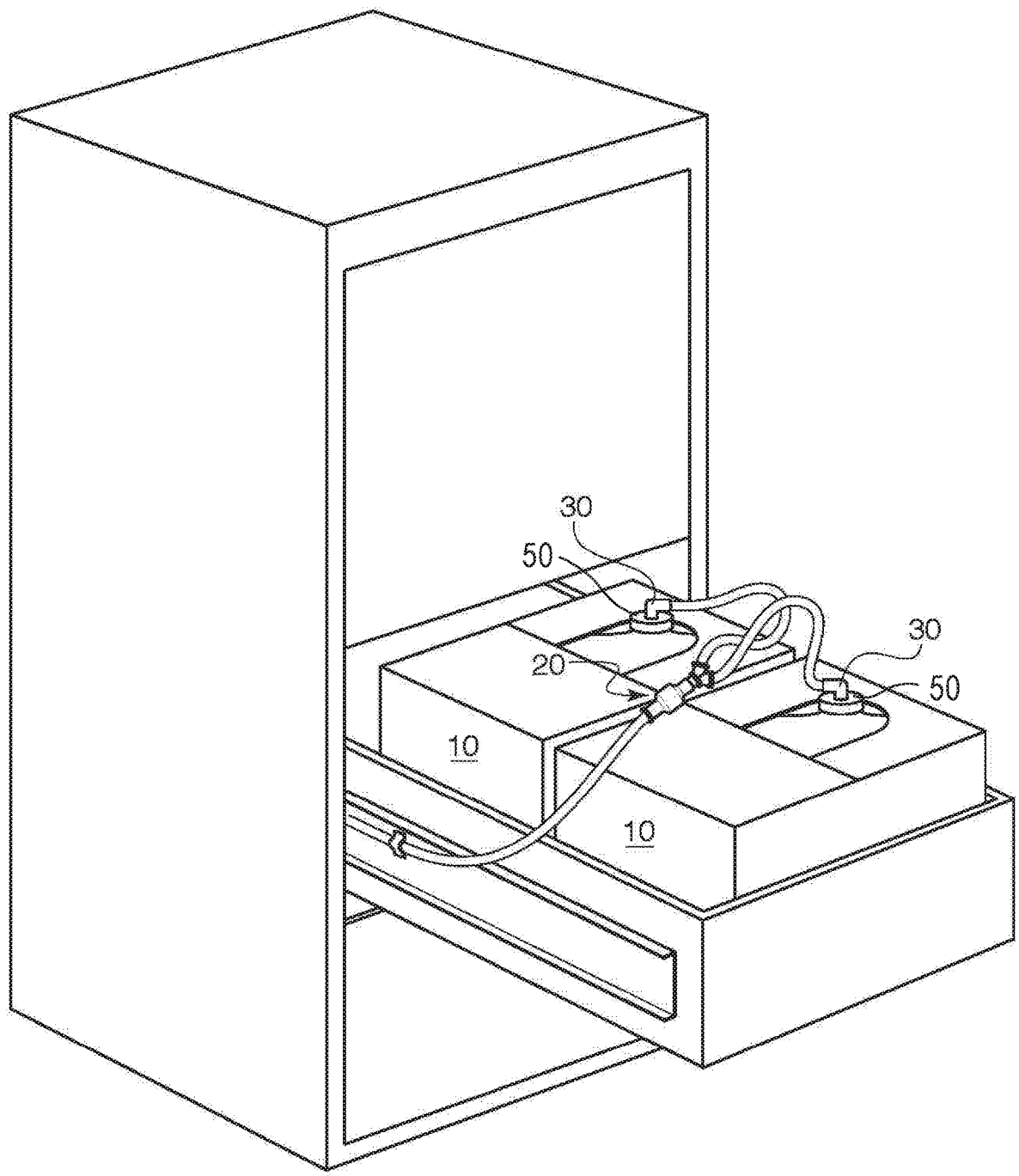
FIG. 6 shows a side perspective view of a reagent container system with secured tubing.
Figure 7:
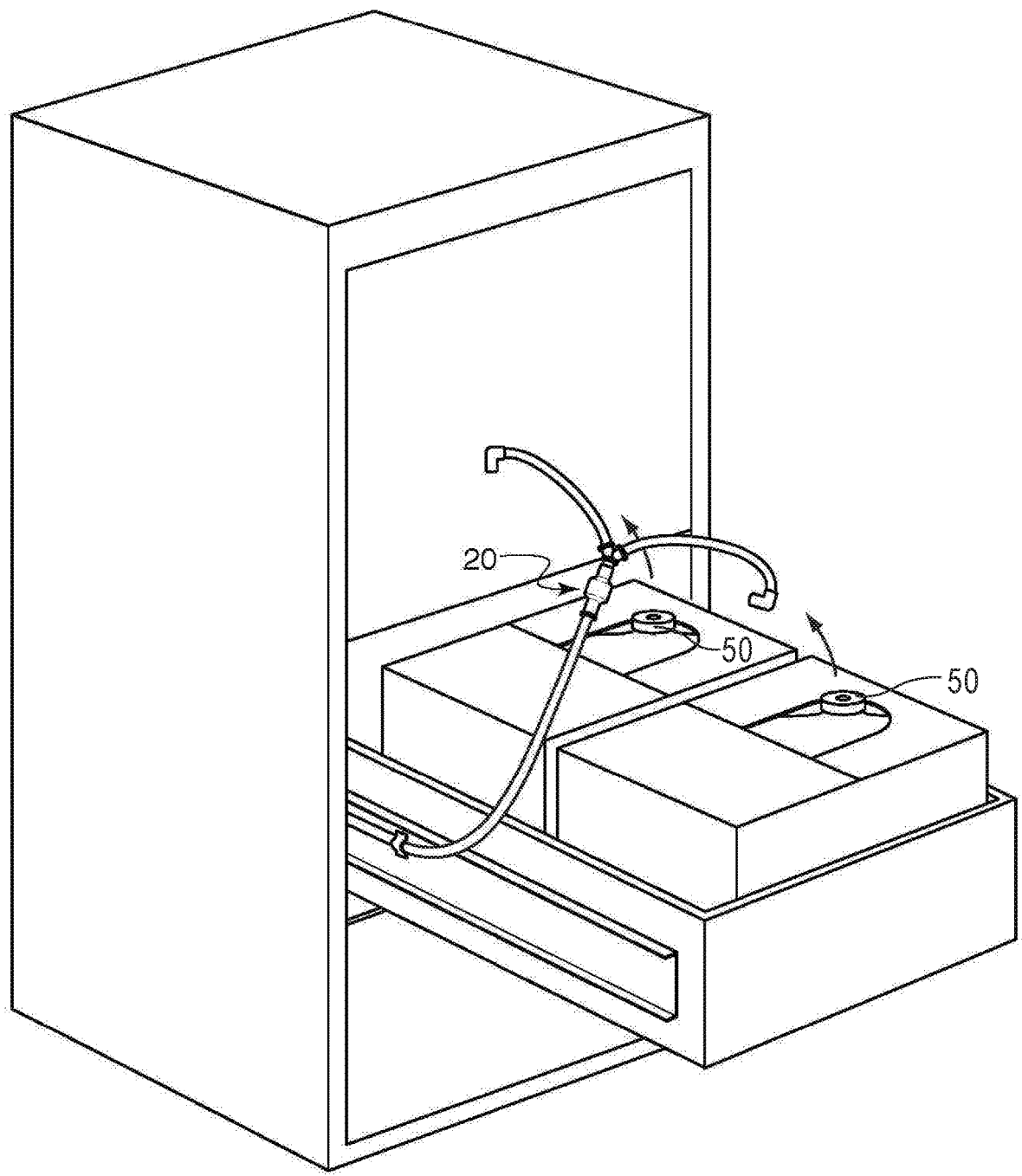
FIG. 7 shows a side perspective view of the system of FIG. 6 with the reagent container tubing removed.
Figure 8:
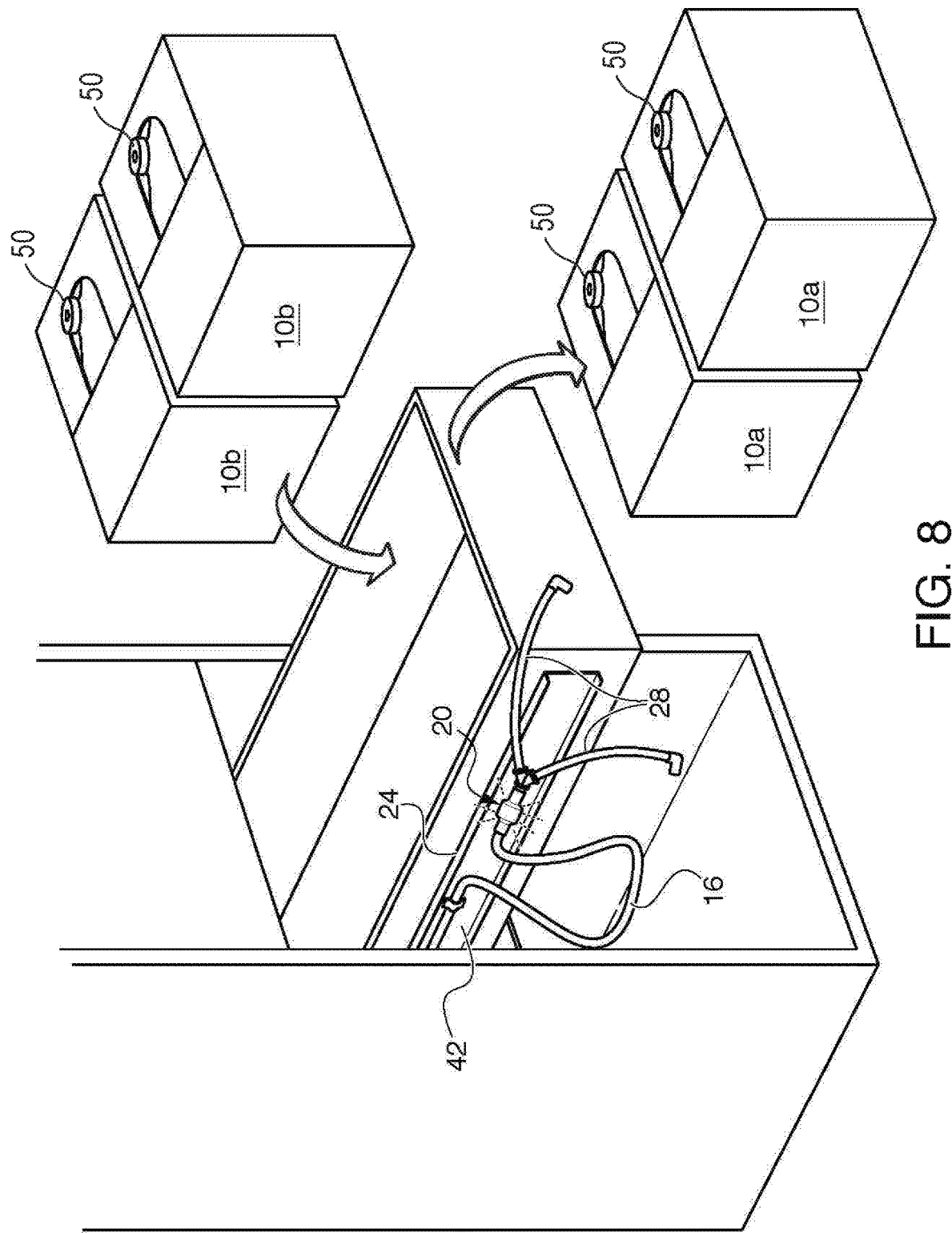
FIG. 8 shows a side perspective view of a magnetic tubing management system described herein in use during exchanging of reagent containers.

It has been found that magnetic tubing management system 20 described herein is superior to previous tubing management attempts, which have included clamps, hooks, and other types of mechanical brackets which take up space and have not met with strong user compliance. By providing the magnetic tubing management system 20 described herein, equipment tubing is better maintained in a sanitary condition. In use, the user may replace reagent connections 30 from containers 10, as illustrated by FIGS. 6 and 7. Then, rather than allowing the reagent connection lines 28 (and accompanying reagent connectors 30) to dangle or drag, and rather than requiring securement via a clamp or a hook, the magnetic system 20 is used to secure the tubing to a magnetically responsive surface 24 as illustrated by FIG. 8.

Figure 9:
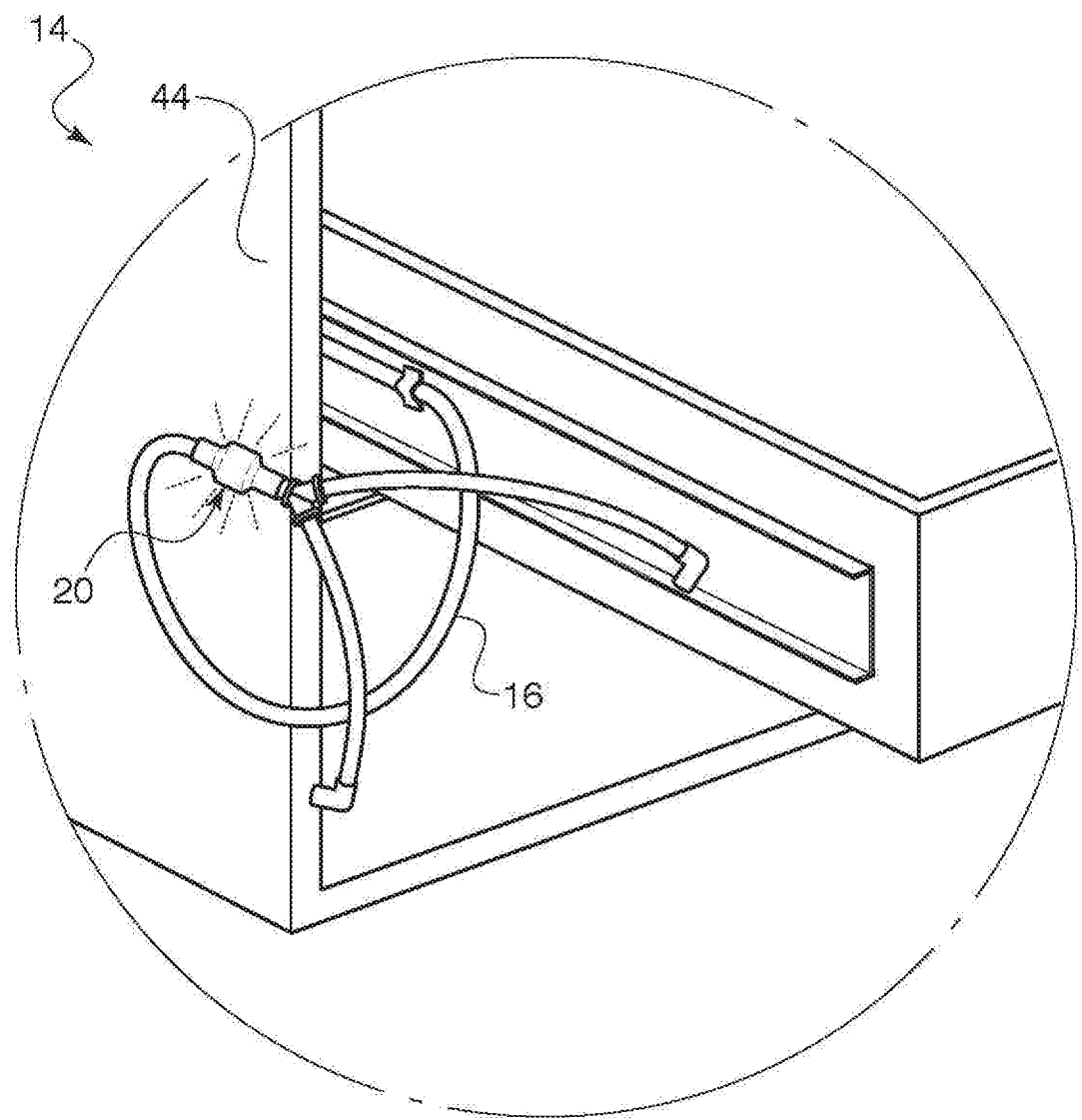
FIG. 9 shows a side perspective view of an alternate anchoring location.

In many instances, the magnetically responsive surface will be a side rail 42 of a drawer 12. However, as illustrated by FIG. 9, the magnetically responsive surface may alternatively be a side wall 44 of an equipment stand or base 14. Additionally, depending upon the length of tubing 16, the magnetic system 20 may be used to secure the tubing to any other appropriate surface, such as a stand door, a benchtop, a keyboard tray, or any other magnetically responsive surface nearby. If there is no inherently magnetic surface within easy reach of the reagent container 10, a small patch of magnetic material can be secured to a non-magnetic surface nearby. For example, a portion or strip of a magnetically responsive material may be adhered to or otherwise secured to or associated with one or more surfaces of the equipment base. When the tubing 16 is secured as described, the user may remove old agent containers 10a and replace them with new reagent containers 10b, all while the tubing 16 is safely anchored off the floor or other potentially contaminated surfaces.

In one embodiment, the magnetically responsive surface to which the one or more magnets is attached may have an indicator to show that the magnet may be secured thereto. For example, a recess in the material may be provided that is sized and shaped to receive the magnet, indicating its use to the user without the need to provide instructions for use. In another example, the surface may be marked with an arrow, a magnetized image, or any other appropriate indicator. In another example, the part of the drawer slide to which the magnet is attached is recessed. The general intent is to provide an ergonomic aid in order to render the system easy for a user to understand and use without the need for detailed instructions.

Although use of a single magnet is primarily described herein, it should be understood that there may be two or more magnets positioned along the length of tubing. This may allow for variation in where the tubing is placed during the reagent container change. Magnets could be positioned to reach various different magnetic surfaces nearby. This may help a user manage longer tubes. It is also possible to provide two or more tubes, each having a magnet. This results in a plurality of tubes in which at least one pair of tubes shares a magnet; or a plurality of tubes in which at least one tube does not share a magnet with any other tube. In some embodiments, the magnet is indirectly associated with the tubing. For example, the magnet may be positioned on the cap 50 of the reagent container.

It should be understood that various different features described herein may be used interchangeably with various embodiments. For example, if one feature is described with respect to particular example, it is understood that that same feature may be used with other examples as well.

Although certain embodiments have been shown and described, it should be understood that changes and modifications, additions and deletions may be made to the structures and methods recited above and shown in the drawings without departing from the scope or spirit of the disclosure or the following claims.

What is claimed is:

1. A tubing management system, comprising:
   a length of tubing associated with laboratory equipment; and
   at least one magnet associated with the length of tubing, wherein the at least one magnet comprises a ring magnet, the ring magnet comprising a protective sleeve that seals both ends of the ring magnet in place on the length of tubing.

2. The system of claim 1, wherein the tubing comprises a Y-portion that connects an equipment line tubing with one or more reagent connection lines, and wherein the at least one magnet is positioned at or near the Y-portion.

3. The system of claim 1, wherein the at least one magnet is positioned anywhere along the length of tubing, at an end of the length of tubing, at a Y-portion of the tubing, or any combination thereof.

4. The system of claim 1, wherein the protective sleeve comprises a heat shrink sleeve.

5. The system of claim 1, wherein the tubing management system is configured to allow a user to securely anchor the tubing to a magnetically responsive surface.

6. The system of claim 5, wherein the magnetically responsive surface comprises a portion of an equipment stand or base; a drawer, stand doors, a benchtop, or a keyboard tray.

7. The system of claim 5, wherein the magnetically responsive surface comprises an indicator.

8. The system of claim 1, wherein the length of tubing is secured only by the at least one magnet and not via a clamp or a hook associated with the equipment.

9. The system of claim 1, wherein a magnetic surface is an inherent magnetic surface of a housing for the laboratory equipment.

10. The system of claim 1, wherein a magnetic surface is a separate magnetically responsive portion of material secured to a surface of a housing for the laboratory equipment.

11. The system of claim 1, wherein the at least one magnet comprises two or more magnets along the length of tubing.

12. A tubing management system, comprising:
   a length of tubing associated with laboratory equipment;
   a ring magnet associated with the length of tubing; and
   a protective covering comprising a heat shrink sleeve positioned over the magnet, wherein the heat shrink sleeve seals both ends of the ring magnet in place on the length of tubing, the tubing comprises a Y-portion that connects an equipment line tubing with one or more reagent connection lines, and wherein the ring magnet is positioned at or near the Y-portion.

13. A method for tubing management for a laboratory instrument positioned on or within an instrument housing, the method comprising:
   providing a first reagent container and a second reagent container;
   providing reagent container tubing with a magnet associated with the tubing, wherein the tubing includes a Y-portion connecting the first and second reagent containers, wherein the magnet comprises a ring magnet, and the ring magnet comprises a protective sleeve that seals both ends of the ring magnet in place on the tubing;
   providing a magnetic surface to attach the magnet to, wherein the protective sleeve seals both ends of the ring magnet in place on the tubing such that a length of the tubing between an instrument connection and the magnet is sufficient to reach the magnetic surface; and
   placing the magnet at the Y-portion such that the first reagent container can be replaced without disturbing the second reagent container;
   wherein placing the magnet includes placing the magnet such that a length of the tubing between the magnet and the connection to the first and second reagent containers is less than a distance between the magnetic surface and the floor.

* * * * *